United States Patent
Sutherland (10) Patent No.: US 8,311,759 B2
(45) Date of Patent: Nov. 13, 2012

(54) INLINE INSPECTION SYSTEM AND METHOD FOR CALIBRATION OF MOUNTED ACOUSTIC MONITORING SYSTEM

(75) Inventor: Jeff Sutherland, Calgary (CA)

(73) Assignee: PII (Canada) Limited, Calgary, Alberta (CA)

( * ) Notice: Subject to any disclaimer, the term of this patent is extended or adjusted under 35 U.S.C. 154(b) by 416 days.

(21) Appl. No.: 12/648,568

(22) Filed: Dec. 29, 2009

(65) Prior Publication Data

US 2011/0161037 A1    Jun. 30, 2011

(51) Int. Cl.
G01D 18/00 (2006.01)
G01H 17/00 (2006.01)
G06F 19/00 (2011.01)
G06F 17/40 (2006.01)

(52) U.S. Cl. ............ 702/104; 73/1.79; 73/1.82; 73/597; 73/865.8; 367/13; 367/117; 367/118; 367/127; 367/129; 702/39; 702/187; 702/189

(58) Field of Classification Search ............. 73/1.01, 73/1.79, 1.82, 570, 584, 592, 596, 597, 602, 73/865.8; 181/139, 142; 367/13, 117, 118, 367/127, 129; 702/1, 33, 35, 39, 50, 51, 702/56, 85, 94, 97, 104, 105, 127, 187, 189; 708/100, 105, 200

See application file for complete search history.

(56) References Cited

U.S. PATENT DOCUMENTS

| | | | |
|---|---|---|---|
| 3,460,028 A * | 8/1969 | Beaver et al. | 324/220 |
| 5,361,636 A | 11/1994 | Farstad et al. | |
| 5,568,449 A | 10/1996 | Rountree et al. | |
| 6,082,193 A * | 7/2000 | Paulson | 73/152.58 |
| 6,243,483 B1 | 6/2001 | Petrou et al. | |
| 6,243,657 B1 * | 6/2001 | Tuck et al. | 702/150 |
| 6,568,271 B2 | 5/2003 | Shah et al. | |
| 6,935,425 B2 * | 8/2005 | Aronstam | 166/250.11 |
| 7,100,463 B2 | 9/2006 | Boudreaux | |
| 2003/0056607 A1 * | 3/2003 | Aronstam | 73/865.8 |

(Continued)

FOREIGN PATENT DOCUMENTS

CA    2313757 A1    7/1999

(Continued)

OTHER PUBLICATIONS

International Search Report mailed Apr. 4, 2011 which issued in Application No. PCT/CA2010/002051.

(Continued)

*Primary Examiner* — Edward Cosimano
(74) *Attorney, Agent, or Firm* — Potomac Patent Group PLLC (57) ABSTRACT

An inline inspection system and method for calibrating an acoustic monitoring structure installed along a pipe. The system includes a pipe inspection vehicle; a microprocessor configured to attach a time stamp to a measured distance traveled by the pipe inspection vehicle; an acoustic source attached to the pipe inspection vehicle and configured to generate sound waves inside the pipe, the sound waves having predetermined frequencies and predetermined amplitudes; plural sensors disposed along the pipe and configured to record time of arrivals and intensities of the sound waves generated by the acoustic source; and a processing unit configured to communicate with the plural sensors and receive the time of arrivals, intensities and frequencies of the sound waves from the plural sensors. The processing unit calibrates the acoustic monitoring structure by calculating a distance between the acoustic source and a first sensor of the plural sensors.

20 Claims, 7 Drawing Sheets

U.S. PATENT DOCUMENTS

| | | | |
|---|---|---|---|
| 2007/0199383 A1* | 8/2007 | Lander et al. | 73/661 |
| 2009/0000381 A1 | 1/2009 | Allison et al. | |
| 2011/0161038 A1* | 6/2011 | Sutherland | 702/103 |

FOREIGN PATENT DOCUMENTS

| | | | |
|---|---|---|---|
| CA | 2636973 A1 | 1/2009 | |
| WO | WO 99/32902 A2 * | 7/1999 | |

OTHER PUBLICATIONS

Written Opinion of the International Searching Authority mailed Apr. 4, 2011 which issued in Application No. PCT/CA2010/002051.

* cited by examiner

800 — Sending a pipe inspection vehicle inside the pipe to travel through the pipe along with a fluid passing through the pipe 802 — Generating sound waves inside the pipe with an acoustic source attached to the pipe inspection vehicle, the sound waves having predetermined frequencies and a predetermined amplitudes 804 — Attaching time stamps to measured distances between the pipe inspection vehicle and a sensor 806 — Recording with plural sensors disposed along the pipe time of arrival, intensities and frequencies of the the sound waves generated by the acoustic source 808 — Receiving at a processing unit the time of arrivals, intensities and frequencies of the sound waves form the plural sensors and the time stamped measured distances 810 — Calibrating the acoustic monitoring structure by calculating a distance between the acoustic source and a first sensor of the plural sensors based on (i) the received time of arrivals of the sound waves at the first sensor, and (ii) measured frequencies and amplitudes of the sound waves received at the plural sensors

INLINE INSPECTION SYSTEM AND METHOD FOR CALIBRATION OF MOUNTED ACOUSTIC MONITORING SYSTEM

BACKGROUND

1. Technical Field

Embodiments of the subject matter disclosed herein generally relate to methods and systems and, more particularly, to mechanisms and techniques for calibrating an acoustic monitoring structure that may be mounted on a piping system.

2. Discussion of the Background

Third-party damage is the leading cause of pipeline failure in the world and accounts for 35-50% of pipeline incidents in the United States and Europe between 1970 and 2001. The damage is especially dangerous because it often goes unreported at the time of occurrence, allowing defects to deteriorate with devastating consequences months or years later, causing safety, environmental and public concern. There is, on average, one delayed failure every 33 days in the US and every 34 days in Europe, resulting from previously unreported third-party damage.

Every impact, large or small, on a pipewall creates acoustic waves that travel upstream and downstream in the pipeline product. Systems are available to provide fully managed, acoustic monitoring for accurate location and immediate risk assessment of impact events to aboveground and underground pipelines.

Such a system (as disclosed by U.S. Patent Application Publication no. 2009/0000381 by Allison et al., known as ThreatScan system from General Electric, 7105 Business Park Road, Houston, Tex., USA) measures the timing and relative magnitude of these waves to determine the impact location and severity. Data is transmitted via satellite to a monitoring center, where the situation is assessed in real time. The system provides fully managed, acoustic monitoring for accurate location and immediate risk assessment of impact events to aboveground and underground pipelines. The owner/operator of the pipeline that has the acoustic monitoring system installed receives notification about potential impact and damage events. Further, the system is capable of assessing the damage and sending results via internet and GSM mobile device to ensure timely notice.

Figure 1:
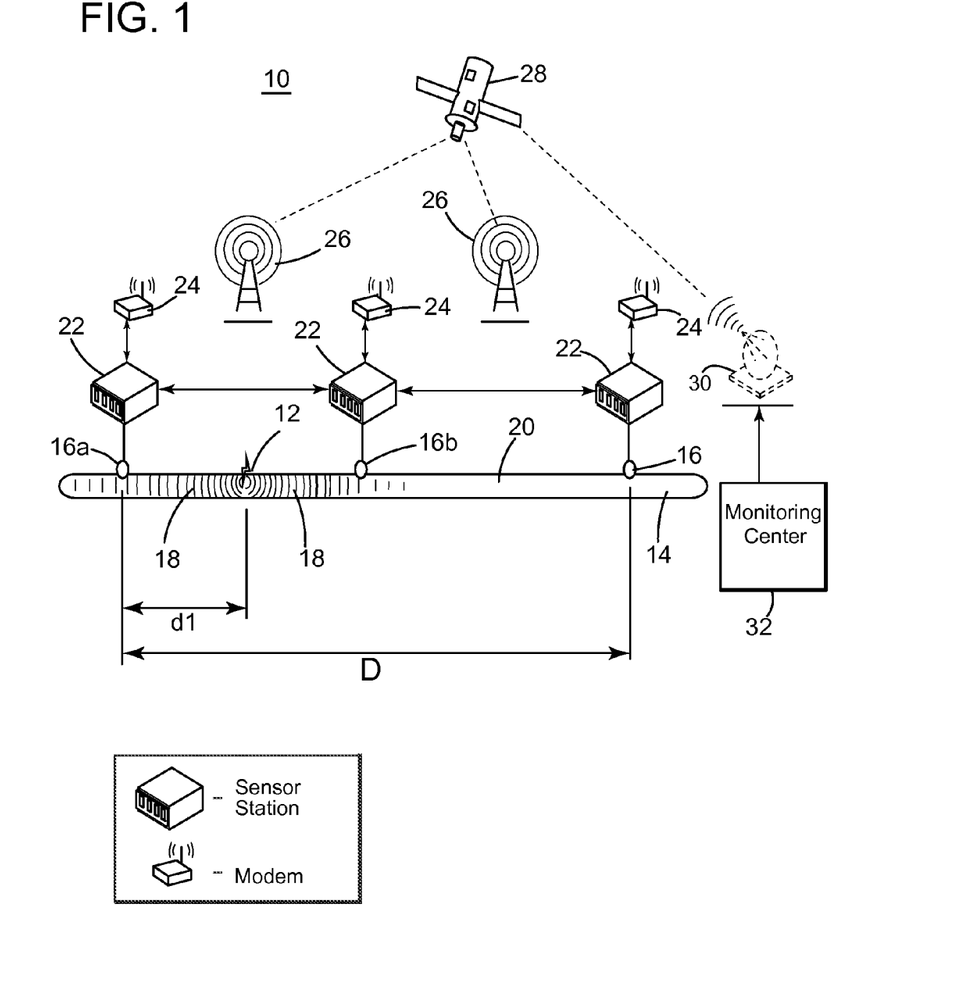
FIG. 1 is a schematic diagram of a conventional acoustic monitoring structure.

More specifically, as shown in FIG. 1, the ThreatScan system 10 is capable to monitor impacts (shocks) 12 occurring to a pipe 14, that may be mounted above or underground. System 10 uses plural sensors 16 spaced apart along pipe 14 for detecting a sound source. Sensors 16 may be spaced between 3 to 21 km apart from each other. A sound source may be the impact 12, which may be produced by the accidental perforation of pipe 14, or other events that may break or not the integrity of pipe 14. Impact 12 generates a sound wave 18 that propagates inside pipe 14. Sound wave 18 propagates in opposite directions to sensors 16a and 16b through a fluid 20 that passes through pipe 14, for example, as shown in FIG. 1. Sensors 16a and 16b are configured to record a time of arrival of wave 18, and/or an intensity of the received wave. In an ideal model and geometry, knowing a distance D between two consecutive sensors 16a and 16b, and a sound speed v in the fluid passing pipe 14, a distance d1 from sensor 16a to impact 12 location may be determined based on formula:

$$d1 = [D(c-u) - \Delta t(c^2 - u^2)]/2c,$$

where c is the sound velocity through the fluid inside the pipe 14, u is the bulk flow velocity of the pipeline fluid, and $\Delta t$ is a transit time difference for the shock to reach sensors 16a and 16b. The transit time difference is equal to T1−T2, where T1 is an arrival time at sensor 16a of a wave generated by the shock and T2 is an arrival time at sensor 16b of the wave generated by the shock. As also shown in FIG. 1, data from sensors 16 are provided to corresponding sensor stations 22 that may include, among other things, a signal processing unit and a power supply (not shown). The sensor stations 22 may communicate through an appropriate modem 24 or other appropriate device with a corresponding base station 26, which in turn may communicate with a satellite 28. Satellite 28 is also configured to communicate with a base station 30, which is in communication with a monitoring centre 32. The monitoring centre receives the data from sensors 16 or the processed data from sensor stations 22 and informs the operator of the centre about a potential damage that occurred in pipe 14 and the location of the damage. More details about the system set up and the procedure used for determining the distance d1 are disclosed in U.S. Patent Application Publication no. 2009/0000381 by Allison et al., the entire content of which is incorporated herein by reference.

However, a problem that can affect the system performance is the accurate determination of the sound path and behavior within the pipeline given the fact that various sections of the pipeline have different characteristics. More specifically, the path and behavior of the sound in the pipe is not known but assumed within current practices. Thus, these assumptions may impact the measured times of arrivals of the sounds at two adjacent sensors and their intensities, thus determining an inaccurate location of the shock impact.

Accordingly, it would be desirable to provide systems and methods that avoid the afore-described problems and drawbacks.

SUMMARY

According to one exemplary embodiment, there is an inline inspection system for calibrating an acoustic monitoring structure installed along a pipe. The system includes a pipe inspection vehicle configured to fit inside the pipe and move through the pipe along with a fluid passing through the pipe; a microprocessor attached to the pipe inspection vehicle and configured to attach a time stamp to a measured distance traveled by the pipe inspection vehicle; an acoustic source attached to the pipe inspection vehicle and configured to generate sound waves inside the pipe, the sound waves having predetermined frequencies and predetermined amplitudes; plural sensors disposed along the pipe and configured to record time of arrivals, intensities and frequencies of the sound waves generated by the acoustic source; and a processing unit configured to communicate with the plural sensors and receive the time of arrivals and intensities of the sound waves from the plural sensors. The processing unit receives the time stamped measured distance travelled by the pipe inspection vehicle and calibrates the acoustic monitoring structure by calculating a distance between the acoustic source and a first sensor of the plural sensors based on (i) the received time of arrivals of the sound waves at the first sensor, and (ii) data stored in a memory of the processing unit.

According to another exemplary embodiment, there is an inline inspection device for calibrating an acoustic monitoring system installed along a pipe. The device includes a pipe inspection vehicle configured to fit inside the pipe and move through the pipe along with a fluid passing through the pipe; a microprocessor attached to the pipe inspection vehicle and configured to attach a time stamp to a measured distance traveled by the pipe inspection vehicle; and an acoustic source attached to the pipe inspection vehicle and configured to generate sound waves inside the pipe. The sound waves have predetermined frequencies and predetermined amplitudes such that plural sensors disposed along the pipe record time of arrivals and intensities of the sound waves generated by the acoustic source and communicate to a processing unit the time of arrivals, intensities and frequencies of the sound waves from the plural sensors. The processor receives the time stamped measured distance travelled by the pipe inspection vehicle and calibrates the acoustic monitoring system by calculating a distance between the acoustic source and a first sensor of the plural sensors based on (i) the received time of arrivals of the sound waves at the first sensor, and (ii) data stored in a memory of the processing unit.

According to still another exemplary embodiment, there is a method for calibrating an acoustic monitoring structure installed along a pipe with an inline inspection system. The method includes sending a pipe inspection vehicle inside the pipe to travel through the pipe along with a fluid passing through the pipe; generating sound waves inside the pipe with an acoustic source attached to the pipe inspection vehicle, the sound waves having predetermined frequencies and predetermined amplitudes; attaching time stamps to measured distances between the pipe inspection vehicle and a sensor; recording with plural sensors disposed along the pipe time of arrivals and intensities of the sound waves generated by the acoustic source; receiving at a processing unit the time of arrivals, intensities and frequencies of the sound waves from the plural sensors; and calibrating the acoustic monitoring structure by calculating a distance between the acoustic source and a first sensor of the plural sensors based on (i) the received time of arrivals of the sound waves at the first sensor, and (ii) measured frequencies and amplitudes of the sound waves received at the plural sensors.

BRIEF DESCRIPTION OF THE DRAWINGS

The accompanying drawings, which are incorporated in and constitute a part of the specification, illustrate one or more embodiments and, together with the description, explain these embodiments. In the drawings.

DETAILED DESCRIPTION

The following description of the exemplary embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to the terminology and structure of an inline inspection system for calibration of a mounted acoustic monitoring structure. However, the embodiments to be discussed next are not limited to these systems, but may be applied to other inspection systems that operate in difficult to reach locations for calibrating other mounted monitoring systems.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Figure 2:
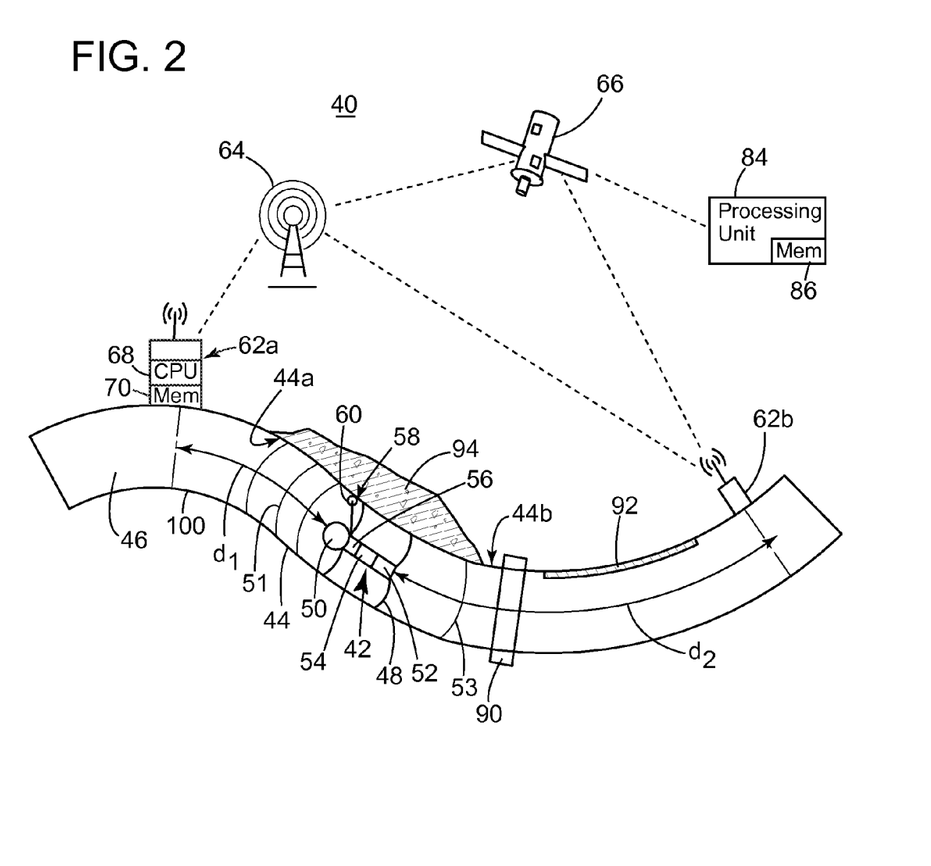
FIG. 2 is a schematic diagram of an acoustic monitoring structure and an inline inspection system according to an exemplary embodiment.

According to an exemplary embodiment shown in FIG. 2, a novel inline inspection system 40 for calibrating an acoustic monitoring structure includes a pipe inspection vehicle 42 that is configured to fit inside a pipe 44. Vehicle 42 is also configured to travel with a fluid flow 46 through the pipe 44 at a same speed as the fluid flow 46. However, in another application, the vehicle 42 is configured to travel at a speed different from the speed of the fluid flow 46 using one of several flow bypass techniques known by those skilled in the art. For having a same speed as the fluid flow 46, the vehicle 42 may have a sealing element 48 that does not allow the fluid flow 46 past the vehicle 42.

An acoustic source 50 may be attached to the vehicle 42. The acoustic source 50 may be a known acoustic sound generator that is capable to generate sound waves 51 and 53 of constant energy in time (constant amplitude), transmit the sound waves at regular time intervals, and/or generate the sound waves to have a predetermined frequency content. More specifically, the predetermined frequency content may include one or more frequencies or a combination of them. In one exemplary embodiment, the frequency content is related to frequencies produced by known impact sources, as for example, drilling the pipe, cutting the pipe, etc. The generated sound waves 51 and 53 propagate in opposite directions along pipe 44 as shown in FIG. 2. By generating waves having predetermined frequencies and amplitudes, the system is able to detect and distinguish these generated waves from real or background waves that might be produced in the pipe and thus, the system is capable of performing a calibration of the various elements measuring and/or calculating the shock 12 with a high accuracy.

Vehicle 42 may include other instruments as known in the art. For example, vehicle 42 may include a power source 52, a processor 54 and other sensors 56, all connected to each other as would be recognized by those skilled in the art. Also, the vehicle 42 may include a precise clock that is configured to furnish time information to the processor 54. Additionally, vehicle 42 may include an odometer device 58 that is configured to measure a distance travelled by the vehicle 42. For example, odometer device 58 may include a wheel 60 that is in direct contact with an inside wall 44a of the pipe 44 and by knowing a number of rotations and a diameter of the wheel 60, processor 54 may accurately calculate the distance travelled by vehicle 42. Processor 54 may add a time stamp to each calculated distance and may store this information in a memory (not shown) for later to be used by processing unit 84. The clock of the vehicle 42 may be accurately synchronized with clocks (GPS clocks) of plural sensors 62a and 62b.

The acoustic monitoring structure includes, among other things, plural sensors 62a, 62b, etc. disposed along pipe 44, on an outside surface 44b of the pipe. A distance between adjacent sensors may vary depending on the application, on the structure of the ground around pipe 44 and other factors but may be between about 2 km and about 30 km. Sensors 62a and 62b and their communication with a base station 64 and/or a satellite 66 have been discussed in detail in the Background section and also in Allison et al. and it is not repeated herein. Each sensor is configured to record time of arrivals and intensities (amplitudes) of the sound waves generated by acoustic source 50 or other acoustic sources. Thus, each sensor may include its own processor 68 and its own storage device (e.g., memory) 70.

The acoustic monitoring structure may also include a central processing unit 84 that collects data from the sensors 62a and 62b and computes, based on that data and other data to be discussed later, a location of the acoustic source or a shock applied to the pipe that generates the acoustic waves. The processing unit 84 also receives the data from the vehicle 42, for example, frequency content and amplitudes emitted by acoustic source 50 and associated times and distances between the sensors and vehicle 42, which are stored as discussed above on the vehicle while the vehicle travels through the pipe. Part or all of the calculations may be distributed in the processing unit 84 and/or individual processors 68 of the sensors. In an exemplary embodiment, the processing unit 84 is configured to communicate with the plural sensors 62a and 62b and receive the time of arrivals and intensities of the sound waves 51 and 53 and to calibrate the acoustic monitoring structure by calculating a distance d1 between the acoustic source 50 and a first sensor 62a of the plural sensors based on (i) the received time of arrivals of the sound waves at the first sensor 62a and the second sensor 62b, adjacent to the first sensor 62a, and (ii) data stored in a memory 86 of the processing unit 84. This data may be the data received from vehicle 42 when vehicle 42 is extracted from the pipe. Also, the data stored in the memory 86 may be geographical locations of the sensors 62a, 62b, their characteristics, the type of fluid and rate of flow that passes through the pipe, a temperature of the fluid, a profile of the pipe, etc.

More specifically, assuming that vehicle 42 travels from the first sensor 62a toward the second sensor 62b, the distance from the vehicle to the sensor 62a is $V_{flow} \cdot T$, where Vflow is the speed of the liquid and T is the time traveled from first sensor 62a to the current position. As such, time-distance and intensity-distance data may be collected as the vehicle 42 travels along pipe 44.

However, it is noted that for the pipe 44 shown in FIG. 2, and in general for pipes provided underground in the field, the length D between two adjacent sensors may not be accurate, the speed c of the sound wave inside the pipe depends on many factors, and a time difference $\Delta T$ between the arrival of the sound waves to the sensors may be affected by a lack of synchronization between clocks of the sensors. As the distance d1 is sensitive to changes in the three quantities D, c and $\Delta T$, a good estimation of distance d1 requires accurate values for these quantities. In this regard, it its noted that the speed c of the sound in the pipe is affected by (i) various fittings mounted on the pipe 44, for example, a valve 90, (ii) various coatings 92 applied to the inside wall 44a of the pipe 44, which act as an acoustic absorber, thus attenuating the waves, and/or (iii) various geological formations 94 neighboring the pipe 44. Other factors that affect an accurate determination of a distance between a source of a shock and the sensors are changes in product (fluid flow) phase and/or density, pipeline environment, constructions around the pipe, etc. All these factors affect the speed c, and intensity A of the sound wave and the traditional inspection devices might not be able to account for these influences.

To account for these factors and influences, the novel vehicle 42 generates the acoustic waves 51 and 53 (simulating a shock applied to pipe 44) and the processor 84 calculates at least the distance d1 based on the measured acoustic wave 51 at the first sensor 62a. Processor 84 may also calculate distance d2 between the acoustic source 50 and the second sensor 62b. Distances d1 and/or d2 may be calculated continuously or at given time intervals as the vehicle 42 travels through pipe 44 and processor 84 may generate, based on the calculated distances and the measured distances (with the odometer device 58) a specific and customized acoustic wave profile of sound propagation in the pipe, for each segment of the pipe. A segment of the pipe is defined later. The settings for calculating the above noted profile may be changed from segment to segment.

Figure 3:
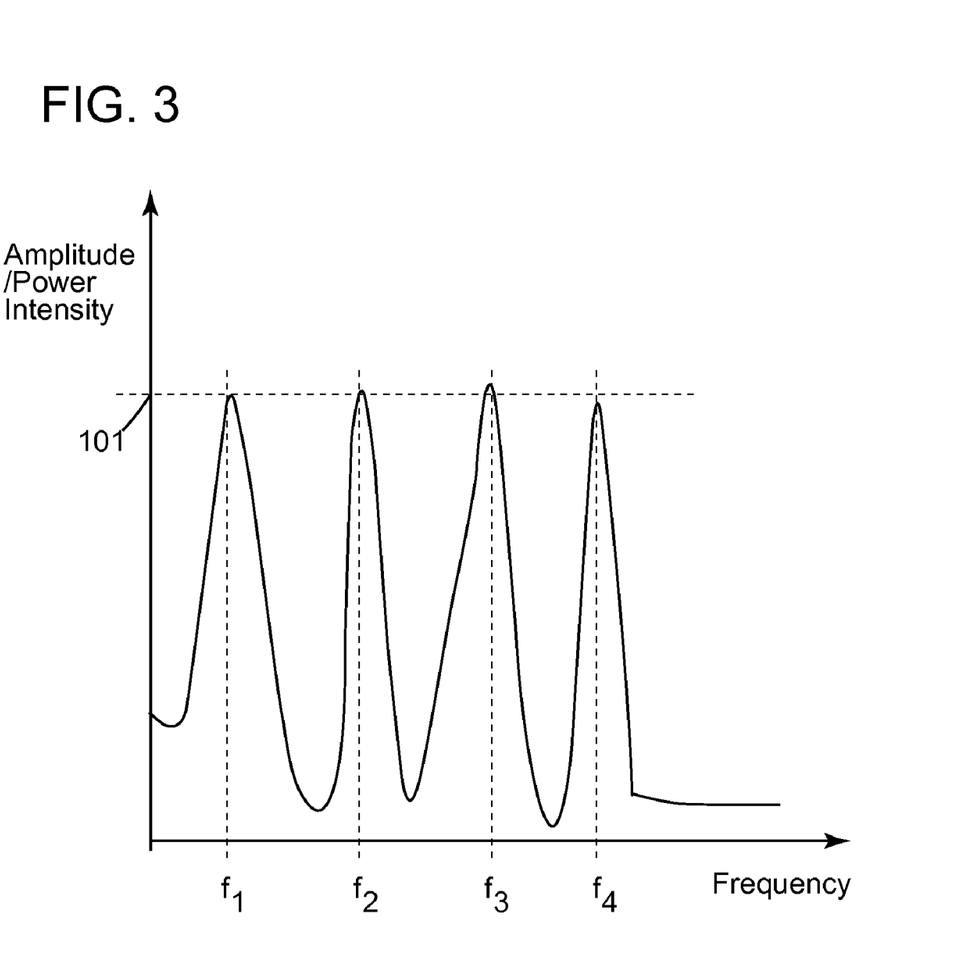
FIG. 3 is a graph showing amplitudes of sound waves versus their frequencies emitted by an acoustic source according to an exemplary embodiment.

A customized acoustic wave profile for a pipe may be generated as shown in FIG. 3. An amplitude of the sound wave emitted by the acoustic source 50 is recorded on the y axis versus the underlying frequency f on the x axis. Four frequencies f1 to f4 are shown in FIG. 3 and these frequencies are selected to be in a frequency band of interest for the operator of the pipe. More or less frequencies may be monitored by the sensors depending on the number of frequencies desired to be emitted by the acoustic source 50. Also, the operator of the vehicle 42, based on the experienced damages to the pipe and associated frequencies may decide which frequencies to be emitted by the acoustic source 50. As seen in FIG. 3, a frequency spectrum is generated by the acoustic source 50 and the spectrum has peaks corresponding to the desired frequencies f1 to f4. A known level 101 of the emitted intensities of the sound waves may be used for calibration purposes. These frequencies are recorded at the plural sensors, where a time stamp is attached by a precision clock. The time stamp is used for later matching the intensities and amplitudes with a position of the vehicle inside the pipe.

Figure 4:
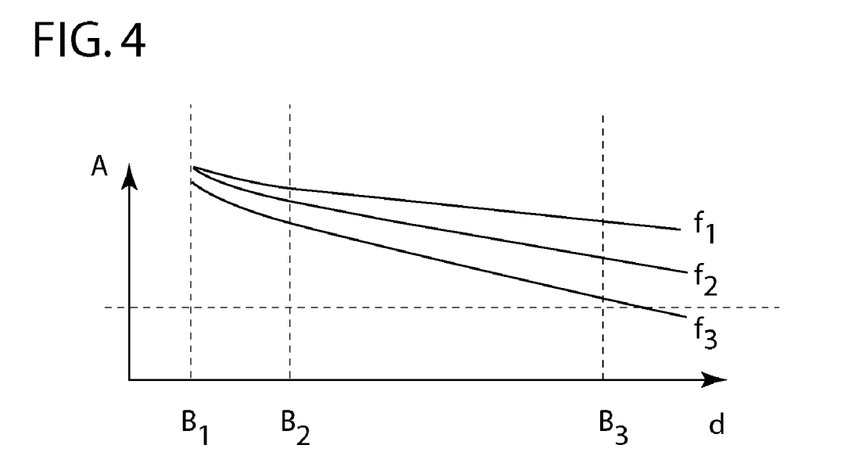
FIG. 4 is a graph showing amplitude attenuation of sound waves versus a distance from the acoustic source.

From the sensors 62a and/or 62b point of view, the frequencies emitted by the acoustic source are affected by the various factors already discussed. Thus, an amplitude of the received frequencies is attenuated as shown in FIG. 4. FIG. 4 shows an amplitude A of the received waves plotted versus a distance d between a sensor and the vehicle 42. The amplitudes of the frequencies f1 to f3 are maximum at position B1, when the vehicle 42 passes the sensor 62a, and then the amplitudes decrease up to a maximum acceptable range at position B3. The position B3 indicates that the amplitude becomes smaller than a sensitivity of the system. A specific feature of the pipe is indicated, for example, by position B2.

Figure 5:
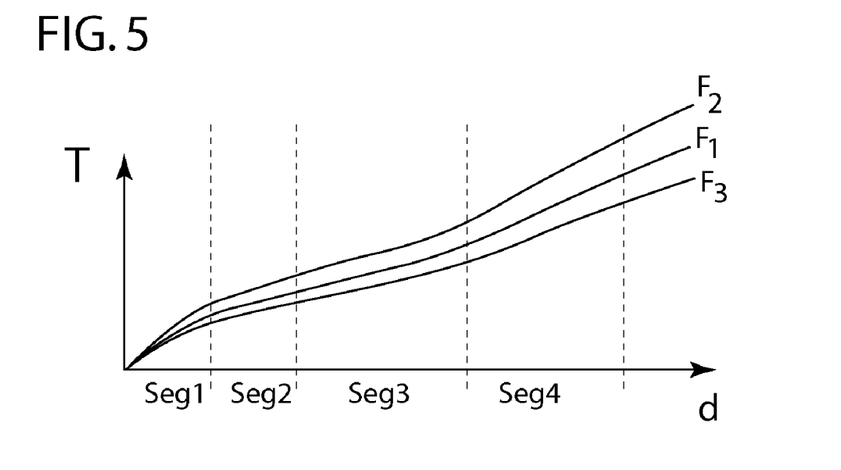
FIG. 5 is a graph showing frequency dispersion of sound waves versus a distance from the acoustic source.

Monitoring the frequencies recorded by the sensor 62a at various times T versus the distance d results in the graph shown in FIG. 5. The frequencies f1 to f3 emitted by the acoustic source 50 are changing as the time passes and the distance from the vehicle 42 increases because of frequency dispersion and other factors as pipeline geometry and pipeline conditions. Another factor that influences the frequency dispersion is the specific characteristics of the various segments of the pipe. The segments of the pipes are illustrated in FIG. 5. The slopes of the curves are exaggerated for clarity.

Figure 6:
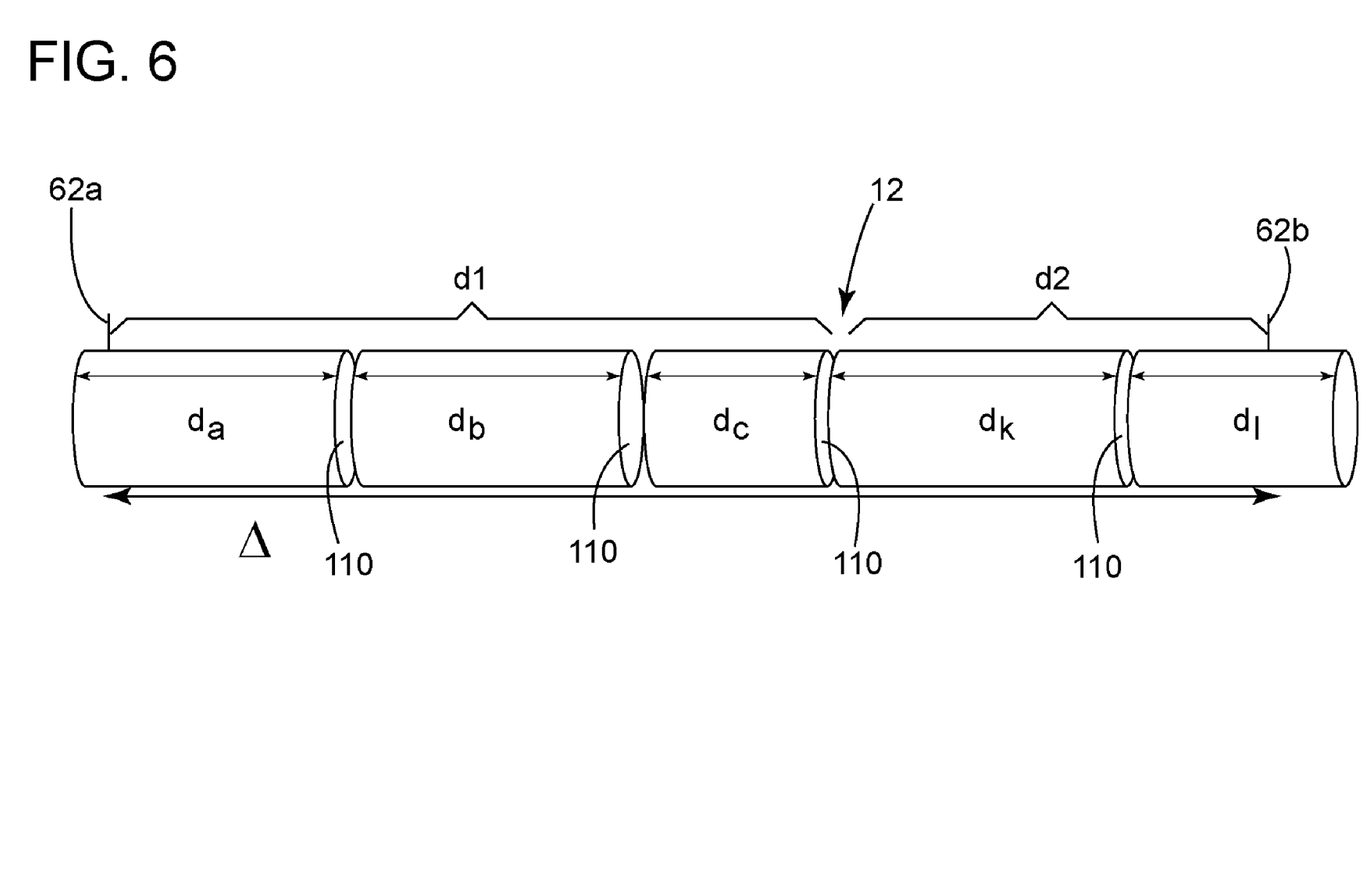
FIG. 6 shows a segmentation of a pipe according to an exemplary embodiment.

The traditional devices are not able to determine the frequency dispersion and the amplitude attenuation. The traditional devices rely on the experience of the operator to account for these phenomena. According to an exemplary embodiment, the pipe investigated by vehicle 42 is divided into segments $d_a$ to $d_f$ (as shown in FIG. 6) based on the calibration discussed above. Each of these segments have common acoustic propagation properties but different from the neighbors segments. Boundaries 110 between the various segments are determined by running the vehicle 42 with the acoustic source 50 on and recording the amplitude and time of arrival of various frequencies emitted by the acoustic source 50 and also by recording a position of the vehicle 42 and a time when the waves are emitted. Changes to the properties of the segments may be due to coatings, pipe geometry (bends, expansions, transitions, etc.) pipe fittings (valves, off take ramps, etc.). These changes may be detected by comparing, for example, a distance measured by the vehicle 42 and stored on board with a distance determined by unit 84 based on the detected frequencies and amplitudes. Thus, the calibration of the plural sensors 62a, 62b (or system 40) may be performed based on the comparison between the actual distance travelled by vehicle 42 and the determined distance traveled by vehicle 42 as calculated by unit 84 based on detected frequencies and amplitudes. The actual distance travelled by vehicle 42 is a linear position that might not take into consideration the actual 3D location of the vehicle. By correlating the measured distance with the determined distance the accuracy of system 40 may be improved and the influences of various factors affecting the pipe and vehicle 42 are taken into account.

For example, by using a known set of frequencies at known distances from the sensors, the segment regions and associated frequencies—velocity performances may be mapped with common characteristics. In one application, considering that each segment has a corresponding speed $c_i$, and there are i segments, each $c_i$ may be mapped as a function of distance d (relative distance from sensor) and time t per segment. As the sound propagates from impact 12 along distances d1 and d2 in FIG. 6, the sound wave travels with different speeds in different segments based on the characteristics of the segments. For this reason, distance d1 may be written as $d1=c_a t_a + c_b t_b + c_c t_c + \ldots$ and distance d2 may be written as $d2=c_k t_k + c_l t_l + \ldots$. This analysis is referred to multisegment analysis. The time t1 necessary for the sound wave to propagate from impact 12 to sensor 62a is given by $t1=\Sigma(t_a, t_b, t_c, \ldots)$ while the time t2 necessary for the sound wave to propagate to sensor 62b is given by $t2=\Sigma(t_k, t_l, \ldots)$. As each $c_i$ has been determined based on the calibration method, it is now possible to determine the attenuation and dispersion of the sound wave more accurately than with traditional methods, in which $\Delta d = d1 - d2 = c \cdot \Delta t$ and $d1 = \frac{1}{2}[D + c\Delta t]$. In this respect, it is noted that based on the calibration method, each $d_i$ and $c_i$ are determined prior to applying the multisegment analysis to a real impact.

Based on the above discussed multisegment analysis, the model traditionally used for calculating the location of the impact may be improved resulting in more accurate results. This analysis may be applied to pipes having a diameter between 6 to 48 in and which are buried under ground or installed above ground. Various mediums, as crude oil, refined products, natural gas, water may be used inside the pipeline together with vehicle 42.

In other words, by performing the calibration of the acoustic monitoring structure, the specific conditions affecting the pipe are taken into consideration, and a better distance between the vehicle 42 and the sensors 62a and 62b may be calculated. In addition, this calibration process takes into account the geometry of the pipe, for example, a bend 100 of pipe 44, and does not affect the transport of a fluid through the pipe.

Figure 7:
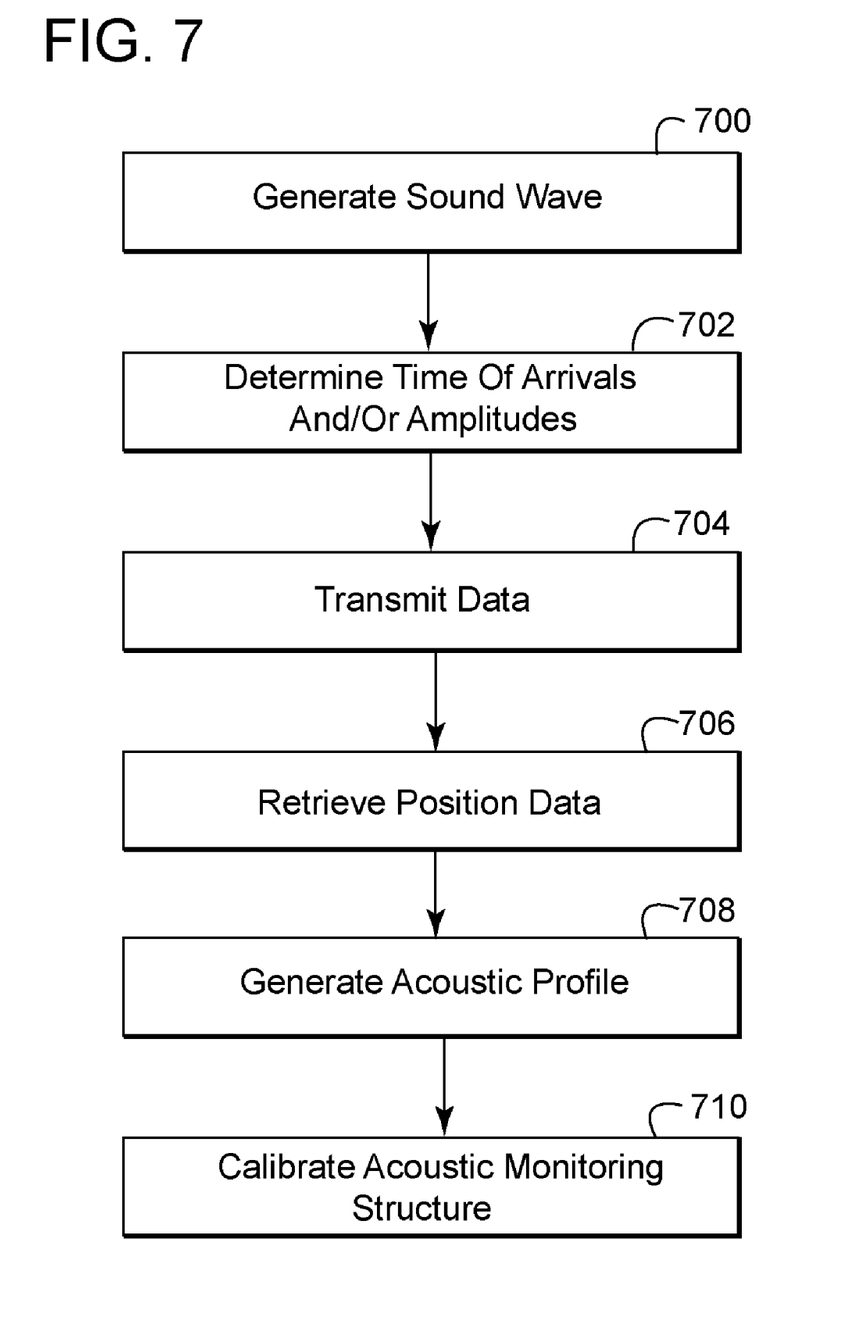
FIG. 7 is a flowchart illustrating steps for calibrating an acoustic monitoring structure with an inline inspection system according to an exemplary embodiment.

Thus, according to an exemplary embodiment illustrated in FIG. 7, a method for direct calibration of the acoustic monitoring structure includes a step 700 of generating a sound wave having a known energy output pulsed at regular time intervals, a step 702 of determining time of arrivals and/or amplitudes of the sound wave at a measuring sensor, a step 704 of transmitting the determined data to a processing unit, a step 706 of retrieving time stamped position data from the vehicle, a step 708 of generating the acoustic wave profile of sound propagation for the inspecting segment of the pipe, and a step 710 of calibrating the sensors and/or the logic for taking into configuration the acoustic wave profile of sound propagation.

According to an exemplary embodiment, the steps of the above method may be performed by adding an appropriate acoustic source to an existing inspection vehicle and by programming appropriately a processor of the acoustic monitoring structure to calibrate the pipe related data based on the data generated by the acoustic source. According to this exemplary embodiment, the acoustic source may be attached to a pipe cleaning device or other pipeline device as long as there is a power source for powering the acoustic source.

According to another exemplary embodiment, the processor 84 may have access to a database, stored for example, in memory 86, that provides geographical coordinates of the pipe for part or its entire length, various characteristics of the pipe, for example, thickness of the wall, material of the wall, etc., distribution of valves and other equipment, for example, compressors, etc.

Figure 8:
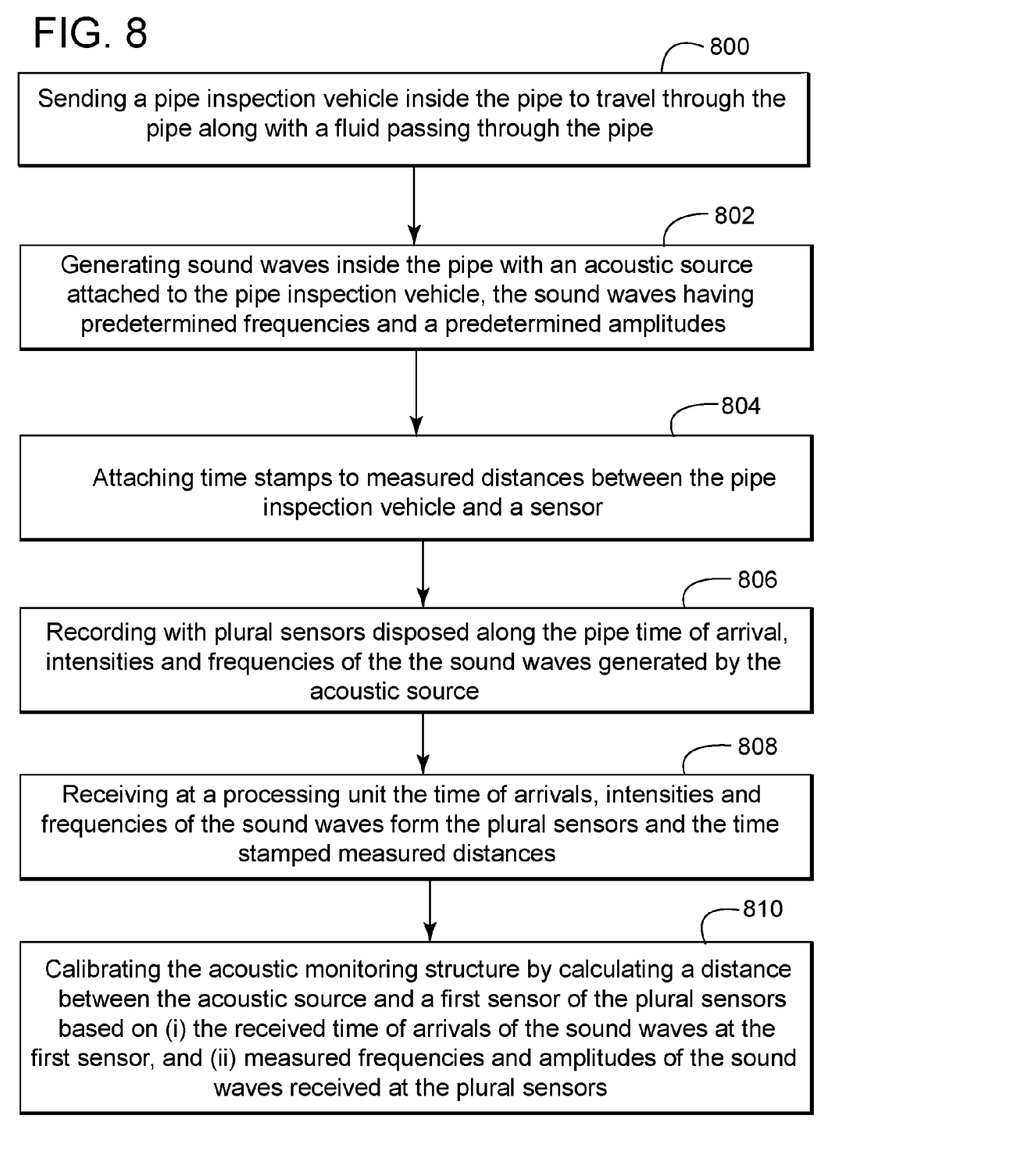
FIG. 8 is a flowchart illustrating steps of a method for calibrating an acoustic monitoring structure according to an exemplary embodiment.

According to an exemplary embodiment shown in FIG. 8, a method for calibrating an acoustic monitoring structure installed along a pipe with an inline inspection system may include a step 800 sending a pipe inspection vehicle inside the pipe to travel through the pipe along with a fluid passing through the pipe, a step 802 of generating sound waves inside the pipe with an acoustic source attached to the pipe inspection vehicle, the sound waves having predetermined frequencies and predetermined amplitudes, a step 804 of attaching time stamps to measured distances between the pipe inspection vehicle and a sensor, a step 806 of recording with plural sensors disposed along the pipe time of arrivals and intensities of the sound waves generated by the acoustic source, a step 808 of receiving at a processing unit the time of arrivals and intensities of the sound waves from the plural sensors and the time stamped measured distances, and a step 810 of calibrating the acoustic monitoring structure by calculating a distance between the acoustic source and a first sensor of the plural sensors based on (i) the received time of arrivals of the sound waves at the first sensor, and (ii) measured frequencies and amplitudes of the sound waves received at the plural sensors.

The disclosed exemplary embodiments provide a system and a method for calibrating an acoustic monitoring structure distributed along a pipe. It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other example are intended to be within the scope of the claims.

What is claimed is:

1. An inline inspection system for calibrating an acoustic monitoring structure installed along a pipe, the system comprising:
   a pipe inspection vehicle configured to fit inside the pipe and move through the pipe along with a fluid passing through the pipe;
   a microprocessor attached to the pipe inspection vehicle and configured to attach a time stamp to a measured distance traveled by the pipe inspection vehicle;
   an acoustic source attached to the pipe inspection vehicle and configured to generate sound waves inside the pipe, the sound waves having predetermined frequencies and predetermined amplitudes;
   plural sensors disposed along the pipe and configured to record time of arrivals, intensities and frequencies of the sound waves generated by the acoustic source; and
   a processing unit configured to communicate with the plural sensors and receive the time of arrivals, intensities and frequencies of the sound waves from the plural sensors and to receive the time stamped measured distance travelled by the pipe inspection vehicle and to calibrate the acoustic monitoring structure by calculating a distance between the acoustic source and a first sensor of the plural sensors based on (i) the received time of arrivals of the sound waves at the first sensor, and (ii) data stored in a memory of the processing unit.

2. The system of claim 1, wherein the acoustic source is configured to transmit signals of constant energy in time.

3. The system of claim 1, wherein the acoustic source is configured to transmit signals at regular time intervals.

4. The system of claim 1, wherein the acoustic source is configured to transmit signals having a predetermined frequency content.

5. The system of claim 1, wherein the processor unit is configured to determine distances between the plural sensors and the acoustic source as the pipe inspection vehicle travels through the pipe.

6. The system of claim 1, wherein the processor unit is configured to generate a specific and customized acoustic wave profile of sound propagation in the pipe for each segment of the pipe based on the time stamped measured distance and the calculated corresponding distance, each segment having similar acoustic properties along its length.

7. The system of claim 1, wherein the processor unit is configured to determine an acoustical attenuation of acoustic energy emitted by the acoustic source through the pipe based on measured distances between the acoustic source and various sensors.

8. The system of claim 1, further comprising:
   an odometer device attached to the pipe inspection device and configured to measure the distance between the acoustic source and the first sensor and to provide the measured distance to the microprocessor.

9. The system of claim 8, wherein the processing unit is configured to receive the time stamped measured distance and adjust one or more of D, c, and $\Delta t$ based on the measured distance and the calculated distance between the acoustic source and the first sensor, wherein D is a distance between the first sensor and a second sensor, c is a speed of the fluid passing through the pipe, and $\Delta t$ is a time difference between detected times of arrivals of the sound waves at the first and second sensors.

10. An inline inspection device for calibrating an acoustic monitoring system installed along a pipe, the device comprising:
    a pipe inspection vehicle configured to fit inside the pipe and move through the pipe along with a fluid passing through the pipe;
    a microprocessor attached to the pipe inspection vehicle and configured to attach a time stamp to a measured distance traveled by the pipe inspection vehicle; and
    an acoustic source attached to the pipe inspection vehicle and configured to generate sound waves inside the pipe, the sound waves having predetermined frequencies and predetermined amplitudes such that plural sensors disposed along the pipe record time of arrivals and intensities of the sound waves generated by the acoustic source and communicate to a processing unit the time of arrivals and intensities of the sound waves from the plural sensors,
    wherein the processor receives the time stamped measured distance travelled by the pipe inspection vehicle and calibrates the acoustic monitoring system by calculating a distance between the acoustic source and a first sensor of the plural sensors based on (i) the received time of arrivals of the sound waves at the first sensor, and (ii) data stored in a memory of the processing unit.

11. The device of claim 10, wherein the acoustic source is configured to transmit signals of constant energy in time.

12. The device of claim 10, wherein the acoustic source is configured to transmit signals at regular time intervals.

13. The device of claim 10, wherein the acoustic source is configured to transmit signals having a predetermined frequency content.

14. The device of claim 10, wherein the acoustic source is configured to generate a specific and customized acoustic wave content in the pipe for each segment defined by two adjacent sensors.

15. The device of claim 10, further comprising:
    an odometer device attached to the pipe inspection device and configured to measure the distance between the acoustic source and the first sensor and to provide the measured distance to the microprocessor.

16. The device of claim 15, wherein the processing unit is configured to receive the time stamped measured distance and to adjust one or more of D, c, and $\Delta t$ based on the time stamped measured distance and the calculated distance between the acoustic source and the first sensor, wherein D is a distance between the first sensor and a second sensor, c is a speed of the fluid passing through the pipe, and $\Delta t$ is a time difference between detected times of arrivals of the sound waves at the first and second sensors.

17. A method for calibrating an acoustic monitoring structure installed along a pipe with an inline inspection system, the method comprising:
    sending a pipe inspection vehicle inside the pipe to travel through the pipe along with a fluid passing through the pipe;
    generating sound waves inside the pipe with an acoustic source attached to the pipe inspection vehicle, the sound waves having predetermined frequencies and predetermined amplitudes;
    attaching time stamps to measured distances between the pipe inspection vehicle and a sensor;

recording with plural sensors disposed along the pipe time of arrivals, intensities and frequencies of the sound waves generated by the acoustic source;

receiving at a processing unit the time of arrivals, intensities and frequencies of the sound waves from the plural sensors and the time stamped measured distances; and calibrating the acoustic monitoring structure by calculating a distance between the acoustic source and a first sensor of the plural sensors based on (i) the received time of arrivals of the sound waves at the first sensor, and (ii) measured frequencies and amplitudes of the sound waves received at the plural sensors.

18. The method of claim 17, wherein the step of generating further comprises:

transmitting the sound waves having constant energy in time;

transmitting the sound waves at regular time intervals; and generating the sound waves to have a predetermined frequency content.

19. The method of claim 17, further comprising:

measuring with an odometer device attached to the pipe inspection device the distance between the acoustic source and the first sensor.

20. The method of claim 19, further comprising:

adjusting one or more of D, c, and $\Delta t$ based on the time stamped measured distances and calculated distances between the acoustic source and the first sensor, wherein D is a distance between the first sensor and a second sensor, c is a speed of the fluid passing through the pipe, and $\Delta t$ is a time difference between detected times of arrivals of the sound waves at the first and second sensors.

* * * * *